US00PP08458P

United States Patent [19]

Schumann

[11] Patent Number: Plant 8,458

[45] Date of Patent: Nov. 9, 1993

[54] GERANIUM PLANT NAMED FISBRA

[75] Inventor: Ingeborg Schumann, Telgte, Fed. Rep. of Germany

[73] Assignee: Florfis AG, Binningen, Switzerland

[21] Appl. No.: 904,330

[22] Filed: Jun. 25, 1992

[51] Int. Cl.[5] ..... A01H 5/00
[52] U.S. Cl. ..... Plt./87.12
[58] Field of Search ..... Plt./87.12

*Primary Examiner*—James R. Feyrer
*Assistant Examiner*—Erich Veitenheimer
*Attorney, Agent, or Firm*—Foley & Lardner

[57] ABSTRACT

A new and distinct cultivar of geranium plant named Fisbra, particularly characterized by the combined features of large single flowers of purple-red color, round flower shape, dark green foliage with good chlorophyll stability, weak zonation, and good tolerance to rain and heat.

1 Drawing Sheet

The present invention comprises a new and distinct cultivar of geranium, botanically known as *Pelargonium zonale*, and hereinafter referred to be the cultivar name Fisbra.

Fisbra was discovered by the inventor Ingeborg Schumann as a mutation in July 1987 growing among a group of stock plants of the parent cultivar Fiswig at Galdar, Gran Canaria, Spain. Fiswig is disclosed in U.S. Plant Pat. No. 7,385, and is characterized by its large single carmine and red flowers and dark green foliage. The inventor observed on one plant of the parent cultivar one truss of flowers having a pink color. A few days later, more buds were open and were similarly pink in color. A large part of the plant had undergone mutation. Several stems bearing the mutative flowers were cut by the inventor and taken to Hillscheid, Federal Republic of Germany. These cuttings were planted, grown out, and subsequently propagated.

The first act of asexual reproduction of Fisbra was accomplished when vegetative cuttings were taken in February 1988 in a controlled environment at Hillscheid, Federal Republic of Germany by the inventor, Ingeborg Schumann.

Horticultural examination of selected units initiated at Hillscheid, Federal Republic of Germany in May 1988 and continuing thereafter has demonstrated that the combination of characteristics as herein disclosed for Fisbra are firmly fixed and are retained through successive generations of asexual reproduction.

Fisbra has not been observed under all possible environmental conditions. The phenotype may vary with variations in environment such as temperature, light intensity and day length, without, however, any variation in the genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Fisbra which in combination distinguish this geranium as a new and distinct cultivar:

1. Vivid purple-red flower color, with a tinge of carmine.
2. Large round flowers of single type.
3. Dark green foliage with good chlorophyll stability and transportation ability.

4. Weak zonation on leaf.
5. Fast rooting ability.
6. Good rain resistance and comparatively litle shattering.
7. Good heat tolerance.

Of the many commercial cultivars known to the present inventor, the most similar in comparison to Fisbra is the parent variety Fiswig. In general comparison to Fiswig, Fisbra has a vivid purple-red (fuchsia) flower color (RHS 57 B-C) compared to the more carmine red or pink color (52A) of Fiswig. A further distinction is that the zonation on the leaves of Fisbra is a little more distinct than on Fiswig. Plant habit and growth characteristics of Fisbra are very close to those of Fiswig.

The accompanying photographic drawing shows typical flower and foliage characteristics of Fisbra, with colors being as true as possible with illustrations of this type. The photograph does not identically depict true flower color, which is accurately identified by the color values noted below.

In the following description color references are made to The Royal Horticultural Society (RHS) Colour Chart. The color values were determined indoors by flowers taken in June from plants grown outdoors at Hillscheid, Federal Republic of Germany.

Classification:

*Botanical.*—A hybrid of the genus *Pelargonium zonale* L'Hert.

*Commercial.*—Zonal geranium cv. Fisbra.

INFLORESCENCE

A. Umbel:

*Average diameter.*—120 mm.
*Average depth.*—70 mm.
*Peduncle length.*—145 mm.
*Pedicel length.*—40 mm.
*Pedicel color.*—Light red, with swelling (knot).
*Number of flowers per umbel.*—About 20–40.

B. Corolla:

*Average diameter.*—45 mm.
*Form.*—Single (5 petals).
*Color (general tonality from a distance of three meters).*—Purple-red with a slight carmine tinge.
*Color of upper side of petal.*—57 B-C; upper petals have a small light spot at the base.
*Color of underside of petal.*—Approximately 57 D.

*Sepals.*—Red at base with green tips.

C. Bud:

*Shape.*—Elongated.

*Color (immature).*—Green, with reddish spot at the base.

*Color (mature).*—Red.

*Pedicels.*—Green, partly light red, with swellings (knots).

D. Reproductive organs:

*Androecium.*—7 anthers, 5 fertile with orange-yellow pollen.

*Gynoecium.*—5 ∝ 6 lobed stigma, reddish style and stigma.

E. Spring flowering response period: In Hillscheid, Federal Republic of Germany in 1989 60% of plants with at least 1 flower opened 13 weeks after planting of unrooted cuttings.

F. Outdoor flower production: The flower count in 1989 in Hillscheid, Federal Republic of Germany indicated between 50 and 60 umbels per plant for May through September observation period.

G. Durability: Rain resistance good, shatter resistance for a single flowering variety comparatively good.

PLANT

A. Foliage:

*Form.*—Round to kidney shaped, not quite closed at the base.

*Margin.*—Bicrenate.

*Diameter of leaf.*—9–10 cm.

*Color (upper surface).*—Medium to dark green, approximately 137A–147A.

*Tolerance to botrytis.*—Good.

B. General appearance and form:

*Internode length.*—Short, approximately 0.5 to 1.0 cm.

*Branching pattern.*—3.0 branches per plant after 13 weeks of growing time from unrooted cuttings.

*Height (in August, based on 25 week old plants).*—27 cm on average.

I claim:

1. A new and distinct cultivar of geranium plant named Fisbra, as illustrated and described.

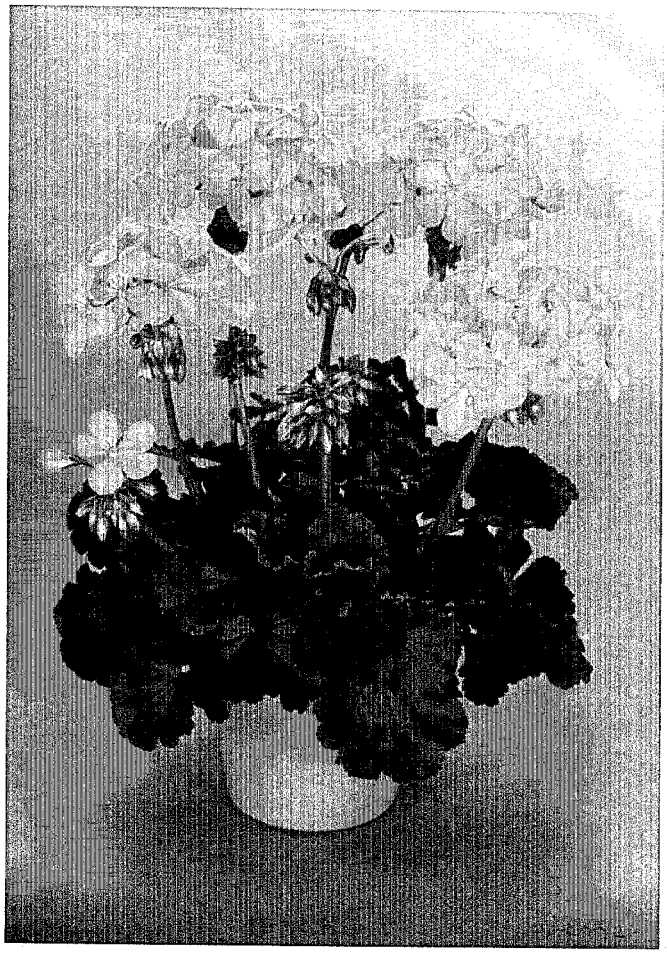

* * * * *